United States Patent [19]

Monte et al.

[11] 4,314,897
[45] Feb. 9, 1982

[54] ELECTROPHORETIC GEL CONTAINER

[75] Inventors: Charles S. Monte, Orange; Wayne S. Johnson, La Habra, both of Calif.

[73] Assignee: Beckman Instruments, Inc., Fullerton, Calif.

[21] Appl. No.: 165,165

[22] Filed: Jul. 1, 1980

[51] Int. Cl.³ .................................... G01N 27/28
[52] U.S. Cl. ......................... 204/299 R; 204/180 R; 23/912
[58] Field of Search ............... 204/180 G, 299 R; 23/230 B

[56] References Cited

U.S. PATENT DOCUMENTS

| | | | |
|---|---|---|---|
| 3,479,265 | 11/1969 | Elevitch | 204/180 |
| 3,523,863 | 8/1970 | Juhos | 204/180 G X |
| 3,622,484 | 11/1971 | Cawley | 204/180 G |
| 3,635,808 | 1/1972 | Elevitch | 204/180 |
| 3,766,047 | 10/1973 | Elevitch | 204/299 |
| 3,767,560 | 10/1973 | Elevitch | 204/299 |
| 3,803,020 | 4/1974 | Stephan | 204/180 G X |
| 3,856,656 | 12/1974 | Brink | 204/180 G X |
| 3,875,045 | 1/1975 | Bergrahm et al. | 204/299 |
| 3,888,759 | 6/1975 | Elson et al. | 204/299 |
| 4,011,350 | 3/1977 | Markovits et al. | 427/2 |

Primary Examiner—Arthur C. Prescott
Attorney, Agent, or Firm—R. J. Steinmeyer; J. E. Vanderburgh; T. R. Schulte

[57] ABSTRACT

An electrophoretic gel container. The device includes a base and a cover. The gel is adherently bound to a backing sheet. The cover is positioned to clamp the backing sheet between it and the base. The cover is spaced from the gel.

7 Claims, 3 Drawing Figures

ELECTROPHORETIC GEL CONTAINER

BACKGROUND OF THE INVENTION

1. Field of the Invention

The invention relates to the field of electrophoretic apparatus. More particularly, the invention is a container for storing and transporting an electrophoretic gel medium. In still greater particularity, the invention is a container which supports a backing sheet to which an electrophoretic gel layer is adhesively attached. By way of further characterization, but not by way of limitation thereto, the invention includes a cover and base for securing a portion of the backing sheet therebetween while maintaining an air space surrounding the gel layer.

2. Description of the Related Art

Electrophoresis involves the placing of a sample substance, such as blood serum or urine, in a support medium across which is maintained a direct current electrical potential. Support media characteristically include: paper; agar; agarose; cellulose acetate and polyacrylamide. The electrical potential causes the colloidal particles in the sample substance to migrate toward one or the other electrodes. The amount of migration is determined by the electrical charges on the particles in the sample substance and the magnitude of the imposed electrical potential. Particles with similar properties tend to group into defined areas and thus a determination can be made as to the amount of each class of substance present in the sample. A graph or analog curve of the relative concentrations of particles can provide information as to the relative proportions of each which are contained in the sample substance. These electrophoretograms provide useful information as to blood serum or urine composition which may be used by clinical pathologists or the like.

It is important to the electrophoretic process that the support medium be uniform and free from imperfections. For example, agarose has been found to be an excellent support medium. The agarose is formed into a gel layer into which the sample substance is placed. An electrical potential is maintained across the gel layer and the particle migrations take place. The gel layer is reacted with a chemical mixture to render the separation visible and readable by a trained individual. Different chemical mixtures may be employed to visualize different classes of separated substances as is known in the art.

A problem which has plagued electrophoretic analysis in the past has been the difficulty of production and maintenance during shipping of the gel layers. That is, due to their chemical composition, the gel layers are difficult to fabricate in situ and thus must be shipped and stored for use by laboratories. The shipping and storage is rendered difficult by the relatively fragile nature of the gel layers. Because the gel layers are very delicate, it is important that suitable protective containers be used. One such container is disclosed in U.S. Pat. No. 3,479,265 issued to F. R. Elevitch on Nov. 18, 1969. In that device, the container includes an upper portion and a lower portion. The lower portion is a flexible sheet which is adhesively attached to the upper portion to form a void space therebetween. The gel substance is injected into this void space and allowed to congeal. The gel is shipped in this container and, when it is desired to utilize the gel layer, the sheet with the gel layer adhering thereto is peeled away from the upper portion.

While suited for its intended purpose, the gel layer may stick to the upper portion and is in constant contact with this upper portion during shipment and storage. Because of this contact, flaws, such as pock marks or cracks, may appear in the gel layer. These flaws are aggravated by shrinkage which is caused by dehydration of the gel layer. In addition, impurities contained on the upper portion contribute to the flaws by marring the surface of the gel layer.

SUMMARY OF THE INVENTION

The invention is a device for containing an electrophoretic gel specimen such as an agarose gel layer. The device includes a backing sheet in adherent contact with the gel layer. The backing sheet is slightly larger than the gel layer such that a portion of the backing sheet extends beyond the perimeter of the gel layer. The backing sheet fits into a base portion which is configured to receive the sheet. A cover portion fits over the gel specimen and contacts that portion of the backing sheet which extends beyond the gel specimen perimeter to secure that contacted portion between the cover and the base. The cover is configured so as not to contact the surface of the gel layer. An airtight container surrounds the base and cover portions to pressure the cover and base against one another and thereby clamp the portion of the backing sheet therebetween. The enclosure is sealed and provides an airtight barrier to prevent both dehydration of the gel layer and intrusion by microbial agents.

DESCRIPTION OF THE PREFERRED EMBODIMENT

Figure 1:
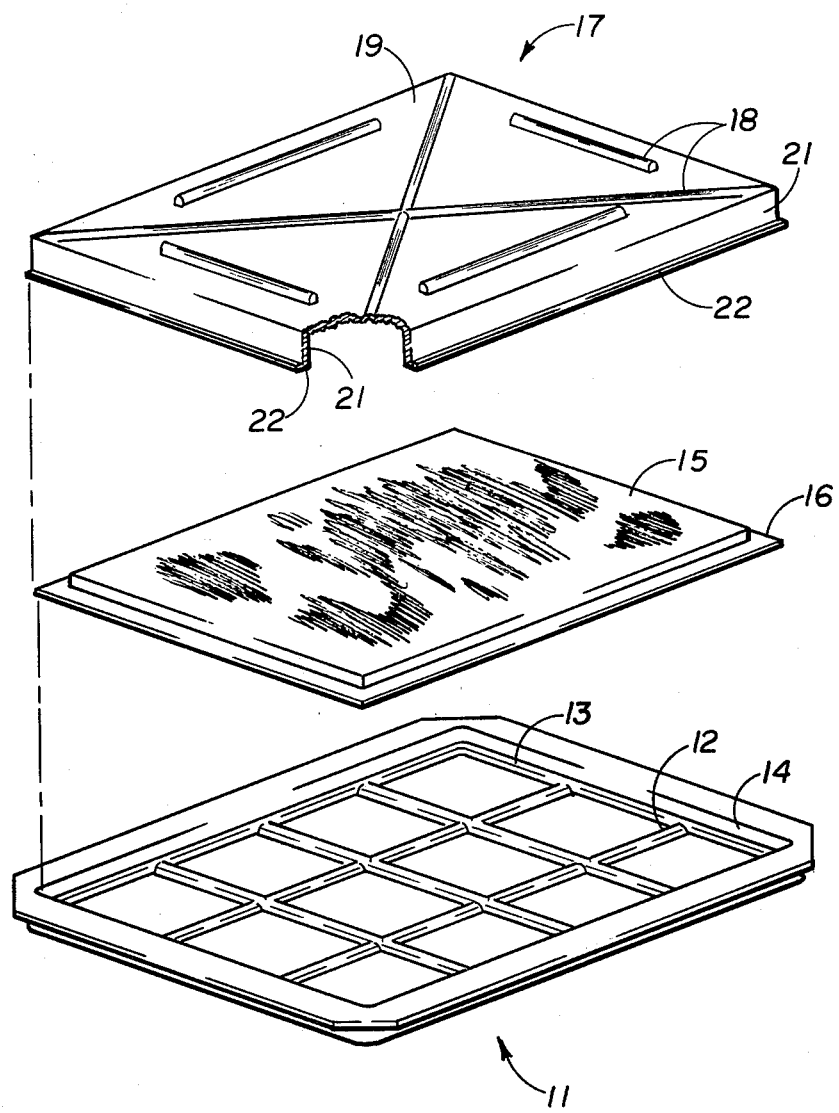
FIG. 1 is a perspective view of the base and cover portions of the container.

FIG. 1 shows a base portion 11 including a plurality of supporting ribs 12 and an outside supporting rim 13. A retaining edge 14 adjoins rim 13. A gel layer 15 is shown in adhesive contact with a backing sheet 16. A cover portion 17 includes a plurality of reinforcing ribs 18 formed on a top surface 19. A wall 21 extends from top surface 19. Wall 21 terminates in compression lip 22. Wall 21 and compression lip 22 comprise a securing means.

Figure 2:
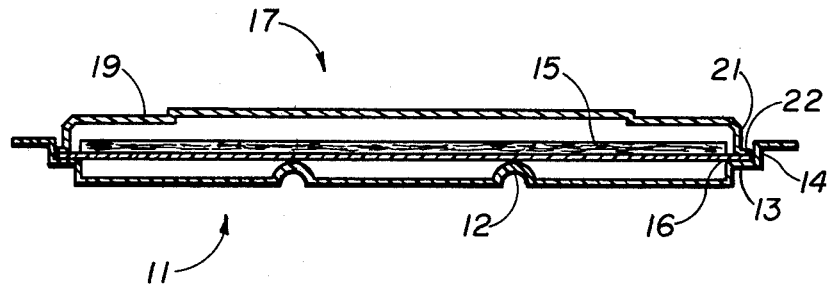
FIG. 2 is a side sectional view of the base and cover portions positioned to maintain the gel layer therebetween.

Referring to FIG. 2, base 11 and cover 17 are shown positioned with gel layer 15 therebetween. Backing sheet 16 is supported by ribs 12 and supporting ridge 13. Wall 21 and compression lip 22 contact backing sheet 16. Compression lip 22 contacts retaining edge 14.

Figure 3:
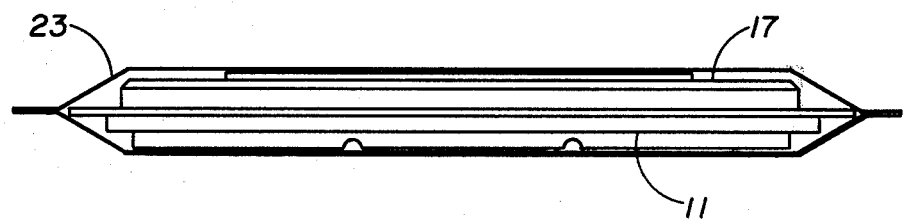
FIG. 3 is a side partially cut-away view of the airtight enclosure illustrating the positioning of the base and cover portions of the container.

Referring to FIG. 3, base 11 and cover 17 are enclosed by an airtight enclosure 23.

Mode of Operation

The manufacturing process for gel layers includes molding of the layer itself. Gel layer 15 is adhesively bound to backing sheet 16 during the molding process. Backing sheet 16 is preferably a clear plastic-type sheet such as that marketed under the trademark "MYLAR" by DuPont. Of course other suitable materials may be utilized as backing sheet 16. Backing sheet 16 is made somewhat larger than gel layer 15 such that a portion of backing sheet 16 extends beyond the perimeter of gel layer 15 as shown in FIG. 1. It is not necessary that backing sheet 16 extend beyond gel layer 15 on all four sides. That is, it would be sufficient if backing sheet 16 extended beyond gel layer 15 on two opposite sides only. Gel layer 15 and backing sheet 16 may be placed in base 11 such that backing sheet 16 rests on supporting ribs 12 and supporting ledge 13. Cover 17 is then placed on base 11. Cover 17 is shown in FIG. 1 with reinforcing ribs 18 suitably formed therein. Because base 11 and cover 17 are preferably made of light-weight plastic material, there is some flexibility in base 11 and cover 17. Supporting ridges 12 in base 11 and reinforcing ridges 18 in cover 17 serve to strengthen the base and cover to reduce this flexibility. Alternatively, base 11 and cover 17 could be made of a relatively rigid material.

Referring to FIG. 2, cover 17 is aligned on base 11 such that walls 21 and compression lip 22 rest on backing sheet 16. Backing sheet 16 is supported on its underside by supporting ridges 12 and supporting ledge 13. In addition to supporting gel layer 15 and backing sheet 16, ridges 12 strengthen base 11 and allow easy removal of backing sheet 16 from base 11. That is, the natural capillary attraction between backing sheet 16 and a planar surface would render removal of backing sheet 16 difficult. The small amount of surface contact between ribs 12 and sheet 16 substantially reduces this difficulty.

The portion of backing sheet 16 which extends beyond gel layer 15 is held between supporting ledge 13, walls 21, and compression lip 22. Gel layer 15 is spaced from walls 21 and from top surface 19 such that only the lower surface of gel layer 15 contacts backing sheet 16 while the rest of gel layer 15 is not contacted by any part of the container. Retaining edge 14 of base 11 cooperates with compression lip 22 to prevent lateral movement of cover 17 on base 11.

Referring to FIG. 3, an airtight enclosure 23 is placed around base 11 and cover 17 so as to contact these portions, thereby pressuring them against each other. Thus, cover 17 is prevented from vertical movement with respect to base 11. Airtight enclosure 23 is preferably a poly/foil bag or the like so as to prevent air transfer therethrough. This prevents dehydration of gel layer 15 during shipping and storage. That is, once an equilibrium point has been reached in the moisture level within airtight enclosure 23, no further dehydration of gel layer 15 will ensue. This moisture-proof sealing arrangement allows a storage life of approximately two years or more for gel layers stored in the present container. This compares with a storage life of six months with many presently used devices.

Because gel layer 15 is not contacted by any surface of the container, the number and severity of pits and pock marks are reduced, thus allowing for a more uniform gel surface. In prior devices the contact of the gel layer with the container aggravated the irregularities in the gel surface in proportion to the length of time which the gel layer was stored in those containers. Because airtight enclosure 23 prevents vertical movement of cover 17 and pressures cover 17 against base 11, backing sheet 16 is securely held in place. That is, the pressure exerted on cover 17 is also exerted on backing sheet 16 where it is contacted by wall 21 and compression lip 22. This pressure serves to clamp backing sheet 16 between compression lip 22 and supporting ledge 13, thereby holding backing sheet 16 in place. Reinforcing ribs 18 in cover 17 and supporting ribs 12 in base 11 allow easy and safe shipping and handling of the container and gel. That is, minimizing the flexibility of top surface 19 and base 11 allows the containers to be stacked and handled without concern that the gel layer will be damaged by contact with top surface 19.

Another advantage of the present invention is that, when it is desired to remove gel layer 15 and backing sheet 16, the removal process may be accomplished easily and without damage to gel layer 15. That is, when airtight enclosure 23 is removed, cover 17 may be easily lifted from base 11. This allows easy access to backing sheet 16 which may then be easily lifted from base 11. Thus, no contact is made between gel layer 15 and any foreign surface. This prevents any contamination or damage to the surface of gel layer 15. Prior devices, such as that disclosed in U.S. Pat. No. 3,479,265 described in the related art section of this application, contacted the gel layer on all surfaces and thus allowed gel layer 15 to at least partially adhere to these surfaces. Removal of the gel layer was thus made more complicated and difficult and damage to the gel layer often resulted.

Other advantages of the present invention include the use of base 11 and cover 17 as an incubation chamber. Incubation must be employed for some gels whose final detection procedure requires that the gel be incubated with a detecting chemical mixture for a specified time. The disclosed container allows this incubation to proceed while protecting the gel and allowing ease of handling. In addition, the container can serve as a humidity chamber which can be employed in certain types of immunological procedures such as immunodiffusion and immunoelectrophoresis. These procedures require incubation of up to several hours and further require that the gel be kept moist. Use of the present invention allows the required humidity to be maintained. Base 11 may also serve as a support for the gel layer during the electrophoresis process. That is, after the gel has been removed and the sample substance placed therein, base 11 may be dried and gel layer 15 and backing sheet 16 returned thereto. Paper wicks may then be affixed to the long edges of gel layer 15. The paper wicks also contact the electrolytic solution and thus electrical contact is maintained between the respective electrodes and gel layer 15.

While particular forms of the invention have been disclosed with respect to a specific embodiment thereof, it is not to be so limited as changes and modifications may be made which are within the full intended scope of the invention as defined by the appended claims. For example, while an agarose gel has been disclosed as gel layer 15, it should be expressly understood that any type of gel may be contained in the present invention. While a gel layer of the shape shown in FIG. 1 is contemplated it should be understood that any shape of gel specimen (spherical, irregular etc.) may be advantageously contained by a suitably shaped container employing the inventive concept disclosed herein. Additionally, it should be expressly understood that airtight enclosure 23 may include elements other than the poly/foil bag disclosed. That is, referring to FIG. 2, cover 17 could be held in place in base 11 by an elastic band or other suitable fastener. Another modification produces an airtight seal by using a sealing substance to contact retaining edge 14 and compression lip 22. This sealing substance could be a strip of wax or the like which also holds cover 17 in place on base 11. The sealing substance could be made to peel off in a strip-like fashion, thereby allowing its easy removal.

The foregoing description, taken together with the appended claims, constitutes a disclosure which enables one skilled in the art and having the benefit of the teachings contained therein to make and use the invention. Further, the structure herein described constitutes a meritorious advance in the art which is unobvious to such skilled workers not having the benefit of these teachings.

What is claimed is:

1. A device for containing an electrophoretic gel specimen, said gel specimen including a lower surface, said device comprising:
    a backing sheet in adherent contact with said lower surface, said sheet having a greater surface area than said contacted lower surface such that at least a portion of said sheet extends beyond said contacted lower surface;
    a base configured to receive said backing sheet; and
    a cover, cooperative with said base and contacting at least a part of said portion to secure said portion between said cover and said base, said cover being spaced from said gel specimen.

2. A device for containing a substantially planar gel layer, said gel layer having a predetermined defined perimeter, said device comprising:
    a backing sheet in adherent contact with at least a portion of said gel layer, said sheet having a greater surface area than said contacted portion such that a portion of said sheet extends beyond said predetermined defined perimeter;
    a base adapted to support said sheet; and
    a cover, alignable with said base to secure said portion of said sheet therebetween, said cover configured so as to be spaced from said gel layer.

3. Device according to claims 1 or 2 further including means for pressuring said cover against said base thereby clamping said portion of said sheet therebetween.

4. Device according to clams 1 or 2 wherein said cover includes:
    a top surface; and
    securing means connected to said top surface, said securing means cooperative with said base for clamping said portion of said sheet therebetween.

5. Device according to claims 1 or 2 further including means, contacting said base and said cover, for sealing said base against said cover.

6. A device for containing a substantially planar gel layer having an upper surface, a lower surface, and edge surfaces, said device comprising:
    a backing sheet in adherent contact with said lower surface, a portion of said sheet extending beyond said edge surfaces;
    a base adapted to receive said sheet; and
    a cover, positioned on said base so as to contain said portion therebetween, said cover being spaced from said upper surface and said edge surfaces.

7. Device according to claims 1, 2 or 6 further including a moisture-proof enclosure enveloping said base and said cover thereby pressing said cover against said base and clamping said portion of said sheet between said base and said cover.

* * * * *

REEXAMINATION CERTIFICATE (576th)
United States Patent [19]
Monte et al.

[11] B1 4,314,897
[45] Certificate Issued  Sep. 30, 1986

[54] ELECTROPHORETIC GEL CONTAINER

[75] Inventors: Charles S. Monte, Orange; Wayne S. Johnson, La Habra, both of Calif.

[73] Assignee: Beckman Instruments, Inc., Fullerton, Calif.

Reexamination Request:
No. 90/000,931, Jan. 6, 1986

Reexamination Certificate for:
Patent No.: 4,314,897
Issued: Feb. 9, 1982
Appl. No.: 165,165
Filed: Jul. 1, 1980

[51] Int. Cl.⁴ ............................................. G01N 27/28
[52] U.S. Cl. ...................... 204/299 R; 204/182.8; 435/809; 435/810; 422/102; 422/61
[58] Field of Search .................. 422/102, 104, 61; 436/46; 435/809, 810, 297, 298; 204/299 R, 182.8

[56]  References Cited
U.S. PATENT DOCUMENTS

| | | | |
|---|---|---|---|
| 2,874,091 | 2/1959 | Fisk | 435/810 X |
| 3,337,416 | 8/1967 | Forgacs | 435/298 X |
| 3,407,133 | 10/1968 | Oliva et al. | 204/299 R |
| 3,479,265 | 11/1969 | Elevitch | 204/180 |
| 3,482,943 | 12/1969 | Csizmas et al. | 422/56 |
| 3,523,863 | 8/1970 | Juhos | 204/180 G X |
| 3,615,006 | 10/1971 | Freed | 206/454 |
| 3,622,484 | 11/1971 | Cawley | 204/180 G |
| 3,635,808 | 1/1972 | Elevitch | 204/180 |
| 3,695,424 | 10/1972 | Cristy et al. | 206/455 |
| 3,710,975 | 1/1973 | Jansen | 220/339 |
| 3,725,004 | 4/1973 | Johnson et al. | 422/102 X |
| 3,756,393 | 9/1973 | Markwitz et al. | 206/456 |
| 3,766,047 | 10/1973 | Elevitch | 204/299 R |
| 3,767,560 | 10/1973 | Elevitch | 204/299 R |
| 3,803,020 | 4/1974 | Stephan | 204/180 G X |
| 3,856,656 | 12/1974 | Brink | 204/180 G X |
| 3,875,045 | 1/1975 | Bergrahm et al. | 204/299 R |
| 3,888,759 | 6/1975 | Elson et al. | 204/299 R |
| 4,011,350 | 3/1977 | Markovits et al. | 427/2 |
| 4,077,515 | 3/1978 | Shoberg | 206/456 |

*Primary Examiner*—John F. Niebling

[57] ABSTRACT

An electrophoretic gel container. The device includes a base and a cover. The gel is adherently bound to a backing sheet. The cover is positioned to clamp the backing sheet between it and the base. The cover is spaced from the gel.

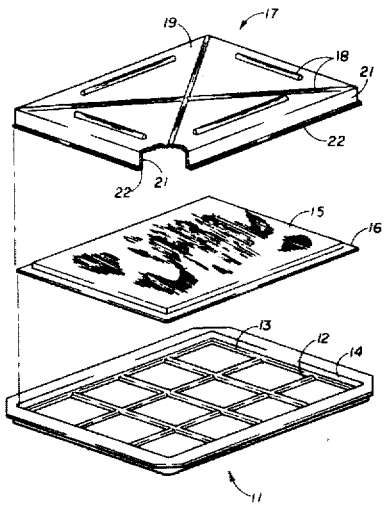

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2 and 6 is confirmed.

Claims 1 and 7 are cancelled.

Claims 3-5 are determined to be patentable as amended.

New claim 8 is added and determined to be patentable.

3. Device according to *claim* [claims 1 or] 2 further including means for pressuring said cover against said base thereby clamping said portion of said sheet therebetween.

4. Device according to *claim* [claims 1 or] 2 wherein said cover includes:
   a top surface; and
   securing means connected to said top surface, said securing means cooperative with said base for clamping said portion of said sheet therebetween.

5. Device according to *claim* [claims 1 or] 2 further including means, contacting said base and said cover, for sealing said base against said cover.

*8. A device for containing an electrophoretic gel wherein the gel comprises a layer of gel material including an upper surface and a lower surface and an edge about its periphery, the device comprising:*
   *a two-sided backing sheet wherein a first side thereof is in adherent contact with the lower surface of the gel, the backing sheet including at least two spaced-apart portions thereof extending beyond the edge of the gel;*
   *a base including a supporting portion adapted to receive and support the second side of the backing sheet; and*
   *a cover including a top member adapted to enclose and be spaced from the upper surface of the gel, and lip members adapted to secure the spaced-apart portions of the backing sheet between the cover and the base.*

* * * * *